(12) United States Patent
Lin et al.

(10) Patent No.: US 12,702,855 B2
(45) Date of Patent: Aug. 11, 2026

(54) ELECTRONIC DEVICE

(71) Applicant: InnoLux Corporation, Miao-Li County (TW)

(72) Inventors: Jih-Ping Lin, Miao-Li County (TW); Chun-Kai Lee, Miao-Li County (TW); Fang-Iy Wu, Miao-Li County (TW); Cheng-Hsu Chou, Miao-Li County (TW)

(73) Assignee: InnoLux Corporation, Miao-Li County (TW)

( * ) Notice: Subject to any disclaimer, the term of this patent is extended or adjusted under 35 U.S.C. 154(b) by 474 days.

(21) Appl. No.: 18/361,338

(22) Filed: Jul. 28, 2023

(65) Prior Publication Data

US 2024/0066313 A1 Feb. 29, 2024

(30) Foreign Application Priority Data

Aug. 30, 2022 (CN) ........................ 202211059478.2

(51) Int. Cl.
*A61N 5/06* (2006.01)

(52) U.S. Cl.
CPC ........ *A61N 5/06* (2013.01); *A61N 2005/0653* (2013.01); *A61N 2005/066* (2013.01); *A61N 2005/0663* (2013.01); *A61N 2005/0664* (2013.01)

(58) Field of Classification Search
CPC .... A61N 2005/0664; A61N 2005/0626; A61N 2005/0645; A61N 2005/0656; A61N 2005/0659; A61N 2005/0662; A61N 5/0616; A61N 5/0613; A61N 2005/0651; G02F 1/13718; G02F 1/167; G02F 1/1675
See application file for complete search history.

(56) References Cited

U.S. PATENT DOCUMENTS

| | | | | |
|---|---|---|---|---|
| 10,709,898 | B2 * | 7/2020 | Mori | A61N 5/0616 |
| 2022/0339461 | A1 * | 10/2022 | Lee | A61N 5/06 |

FOREIGN PATENT DOCUMENTS

| | | | |
|---|---|---|---|
| CN | 106039579 | A | 10/2016 |
| CN | 107049254 | A | 8/2017 |
| CN | 108472495 | A | 8/2018 |
| TW | 201947294 | A | 12/2019 |
| TW | 202016615 | A | 5/2020 |

* cited by examiner

*Primary Examiner* — Elmito Breval
(74) *Attorney, Agent, or Firm* — MUNCY, GEISSLER, OLDS & LOWE, P.C.

(57) ABSTRACT

An electronic device includes a light emitting layer, a light conversion layer and an adjustable structure. The light emitting layer has a plurality of light emitting units for emitting light. The light conversion layer converts the wavelength of the light emitted by at least one light emitting unit to provide converted light. The adjustable structure is controlled to adjust a light penetrating area to correspond to the affected part to be treated, wherein at least one of the light and the converted light passes through the light penetrating area to irradiate the affected part.

18 Claims, 6 Drawing Sheets

ELECTRONIC DEVICE

CROSS-REFERENCE TO RELATED APPLICATIONS

This application claims the benefits of the Chinese Patent Application Serial Number 202211059478.2, filed on Aug. 30, 2022, the subject matter of which is incorporated herein by reference.

BACKGROUND

Field of the Disclosure

The present disclosure relates to an electronic device for performing phototherapy on an affected part.

Description of Related Art

Currently, the important parameters of electronic devices used in phototherapy to treat affected areas include wavelength, optical power density, full width at half maximum, and coherence. However, for existing light sources that can be used in phototherapy, such as semiconductor lasers and light emitting diodes (LED), it is not easy to adjust the wavelengths. Due to the adjustment of materials, processes and structures, the wavelength of light used for phototherapy is typically limited to a few specific wavelengths. However, in the practical application of phototherapy, the wavelength bands that can be absorbed by the photoreceptors (such as chromophores in cells) in different treatment targets (affected parts) are not exactly the same, and thus the limitation of wavelength will lead to poor efficacy of phototherapy. Furthermore, if the application of phototherapy requires more than two types of light, it is necessary to arranged two types of light emitting elements with different wavelengths at the same time, which will increase the pitch between the light emitting elements and thus seriously affect the uniformity of light.

In addition, the current phototherapy is mainly performed on a large area of the human body, without having the capability to irradiate only on the shape of a specific target. Therefore, there is a concern about side effects in healthy areas. If performing phototherapy on a specific area with a method of forming a surface with multiple laser points, it may encounter the disadvantages of poor uniformity and time-consuming, which cannot satisfy the actual requirements.

Therefore, it is desired to provide an improved electronic device to mitigate and/or obviate the aforementioned problems.

SUMMARY

An object of the present disclosure is to provide an electronic device to solve the problems in the prior art.

To achieve the object, there is provided an electronic device for treating an affected part, which includes: a light emitting layer having a plurality of light emitting units for emitting light; a light conversion layer for converting wavelength of light emitted by at least one of the light emitting units to provide converted light; and an adjustable structure controlled to adjust a light penetrating area to correspond to the affected part to be treated, wherein at least one of the light and the converted light passes through the light penetrating area to irradiate the affected part.

Other novel features of the disclosure will become more apparent from the following detailed description when taken in conjunction with the accompanying drawings.

DETAILED DESCRIPTION OF EMBODIMENT

Figure 1:
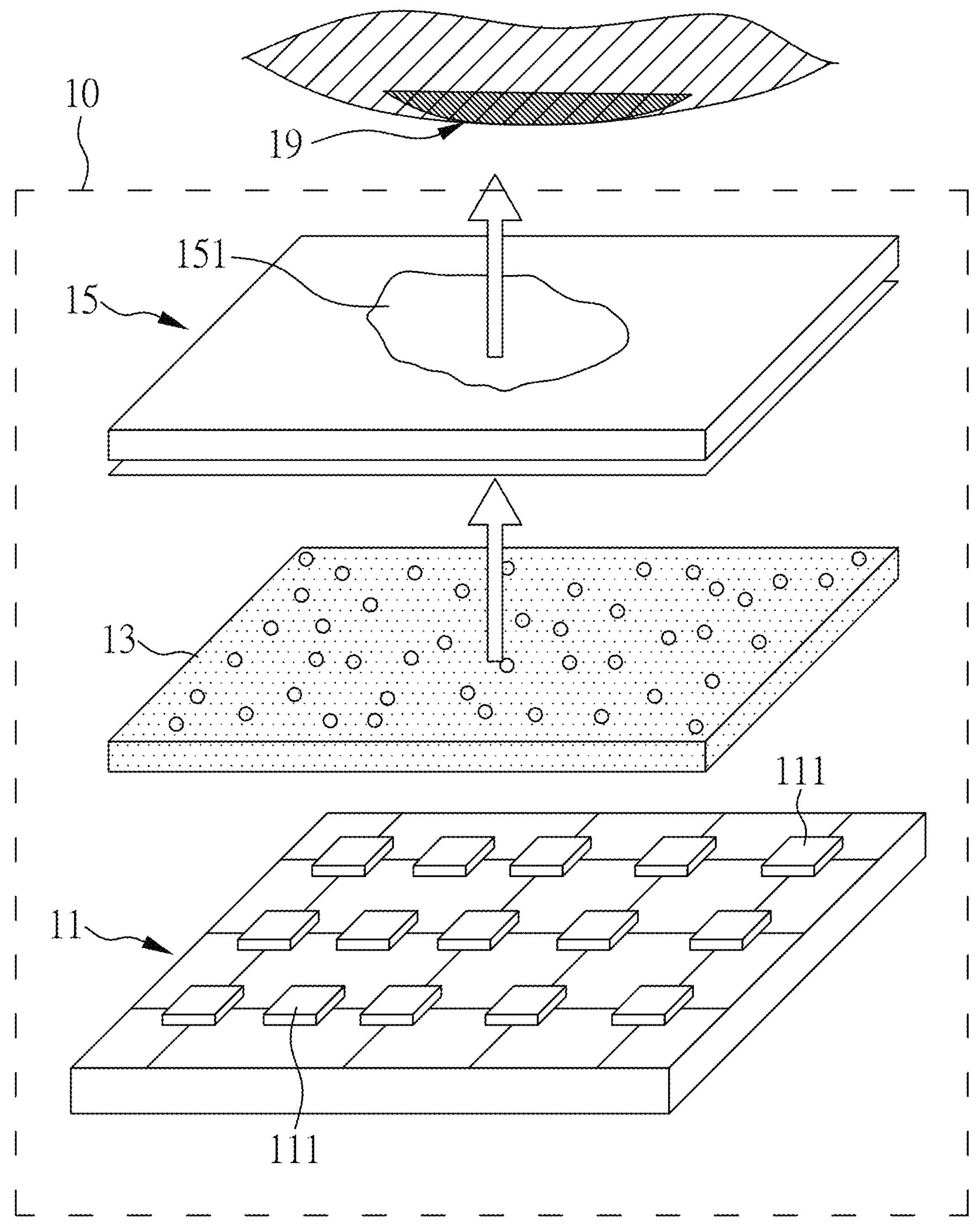
FIG. 1 is a schematic diagram of the electronic device according to an embodiment of the present disclosure.

Different embodiments of the present disclosure are provided in the following description. These embodiments are meant to explain the technical content of the present disclosure, but not meant to limit the scope of the present disclosure. A feature described in an embodiment may be applied to other embodiments by suitable modification, substitution, combination, or separation.

It should be noted that, in the present specification, when a component is described to "comprise", "have", "include" an element, it means that the component may include one or more of the elements, and the component may include other elements at the same time, and it does not mean that the component has only one of the element, except otherwise specified.

Moreover, in the present specification, the ordinal numbers, such as "first" or "second", are only used to distinguish a plurality of elements having the same name, and it does not means that there is essentially a level, a rank, an executing order, or an manufacturing order among the elements, except otherwise specified. The ordinal numbers of the elements in the specification may not be the same in claims. For example, a "second" element in the specification may be a "first" element in the claims.

In the present specification, except otherwise specified, the feature A "or" or "and/or" the feature B means only the existence of the feature A, only the existence of the feature B, or the existence of both the features A and B. The feature A "and" the feature B means the existence of both the features A and B.

Moreover, in the present specification, the terms, such as "top", "upper", "bottom", "front", "back", or "middle", as well as the terms, such as "on", "above", "over", "under", "below", or "between", are used to describe the relative positions among a plurality of elements, and the described relative positions may be interpreted to include their translation, rotation, or reflection.

Furthermore, the terms recited in the specification and the claims such as "above", "over", "on", "below", or "under" are intended that an element may not only directly contacts other element, but also indirectly contact the other element.

Furthermore, the term recited in the specification and the claims such as "connect" is intended that an element may not only directly connect to other element, but also indirectly connect to other element. On the other hand, the terms recited in the specification and the claims such as "electrically connect" and "couple" are intended that an element may not only directly electrically connect to other element, but also indirectly electrically connect to other element.

In the present specification, except otherwise specified, the terms (including technical and scientific terms) used herein have the meanings generally known by a person skilled in the art. It should be noted that, except otherwise specified in the embodiments of the present disclosure, these terms (for example, the terms defined in the generally used dictionary) should have the meanings identical to those skilled in the art, the background of the present disclosure or the context of the present specification, and should not be read by an ideal or over-formal way.

FIG. 1 is a schematic diagram of the electronic device 10 according to an embodiment of the present disclosure. The electronic device 10 is used to treat an affected part 19. The electronic device 10 includes a light emitting layer 11, a light conversion layer 13 and an adjustable structure 15. The light emitting layer 11 has a plurality of light emitting units 111 for emitting light. The light conversion layer 13 may convert the wavelength or color of the light emitted by at least one light emitting unit 111 to provide a converted light. For example, the peak wavelength corresponding to the light emitted by the light emitting units 111 before passing through the light conversion layer 13 is different from the peak wavelength corresponding to the light after passing through the light conversion layer 13, or the color of the light emitted by the light emitting units 111 before passing through the light conversion layer 13 may be different from the color of the light after passing through the light conversion layer 13. The adjustable structure 15 may be controlled to adjust a light penetrating area 151 to correspond to the affected part 19 to be treated, wherein the aforementioned light and/or converted light may pass through the light penetrating area 151 to irradiate the affected part 19.

In this embodiment, the light conversion layer 13 is arranged between the light emitting layer 11 and the adjustable structure 15. That is, the light conversion layer 13 is disposed on the light emitting layer 11, the light emitting surface of the light emitting layer 11 faces the light conversion layer 13, and the adjustable structure 15 is disposed on the light conversion layer 13.

Figure 2A:
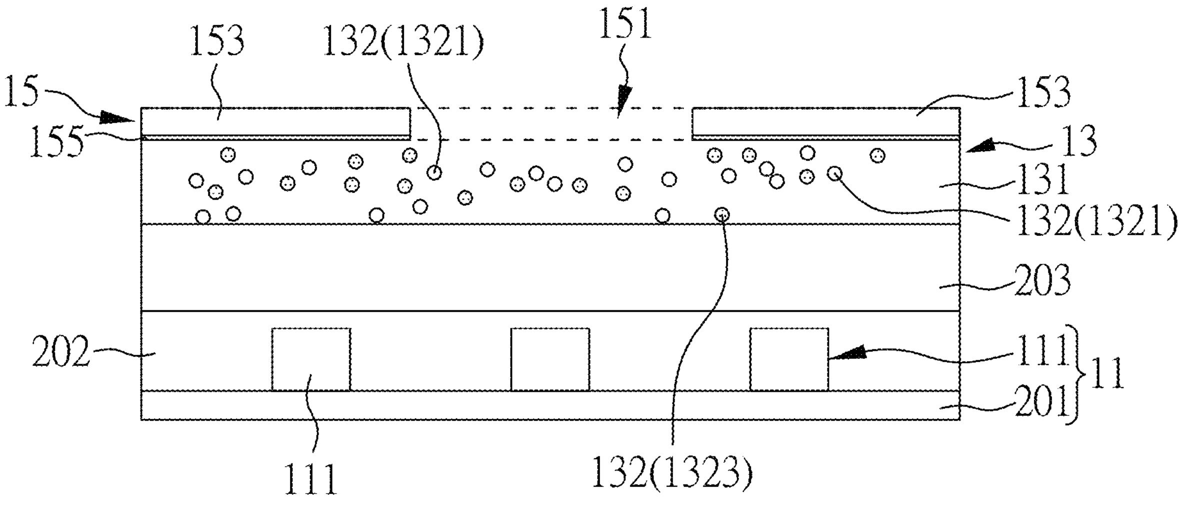
FIG. 2A shows an embodiment of the light emitting layer, the light conversion layer and the adjustable structure realized according to the electronic device of FIG. 1.

FIG. 2A shows an embodiment of the light emitting layer 11, the light conversion layer 13 and the adjustable structure 15 realized according to the electronic device of FIG. 1 of the present disclosure. As shown, in this embodiment, the light emitting layer 11 includes a plurality of light emitting units 111 and a substrate 201, wherein the plurality of light emitting units 111 are arranged in an array, for example, and the light emitting units 111 may be light emitting elements that can emit light, such as light emitting diodes (LEDs) or organic light emitting diodes (OLEDs), while the wavelength of the light emitted is about 250 nm to 900 nm, but the present disclosure is not limited thereto. The plurality of light emitting units 111 are arranged on the substrate 201 and, in order to protect the light emitting units 111, the present disclosure is further provided with an encapsulation layer 202 for encapsulating the light emitting units 111. The encapsulation layer 202 may be acrylic/silicone based material, epoxy material, etc. In addition, in order to firmly connect the light emitting layer 11 and the encapsulation layer 202 to the light conversion layer 13, the present disclosure may further include a connection layer 203 arranged between the encapsulation layer 202 and the light conversion layer 13, and the material of the connection layer 203 depends on the encapsulation layer 202, for example, it may be acrylic/silicone based material, but the present disclosure is not limited thereto.

The light conversion layer 13 includes, for example, a host material 131 and a plurality of light conversion particles 132, wherein the plurality of light conversion particles 132 may be distributed in the host material 131, but it is not limited thereto. The host material 131 may be, for example, a polymer material such as resin, and the light conversion particles 132 may be used to convert the wavelength or color of light, but it is not limited thereto. The light conversion particles 132 may include, for example, quantum dots, phosphorescent materials, fluorescent materials, other suitable materials, or a combination thereof. Since the light conversion particles 132 may convert the wavelength of the light emitted by the light emitting units 111, it is able to generate the converted light in the band required for phototherapy, wherein the wavelength of the converted light ranges from 520 nm to 1100 nm, which can satisfy the requirements of various phototherapy.

Furthermore, based on the principle of light conversion, the wavelength of the converted light obtained from conversion of light depends on the types of the light conversion particles 132. The types of the light conversion particles 132 may be classified, for example, according to the particle sizes of different quantum dots. For example, the quantum dots with larger particle sizes may convert light into converted light with a longer peak wavelength, while quantum dots with smaller particle sizes may convert light into converted light with a shorter peak wavelength, but it is not limited thereto. Therefore, by arranging different types of light conversion particles 1321, 1323 in the host material 131, it is able to generate converted light with different wavelengths. For example, in one embodiment of the present disclosure, the light emitting units 111 emits blue light, for example. The converted light obtained from converting the blue light by the light conversion particles 1321 is near-infrared light, and the converted light obtained from converting the blue light by the light conversion particles 1323 is infrared light. Therefore, by arranging different types of light conversion particles 1321, 1323 in the host material 131, the converted light may include light of two or more peak wavelengths. In addition, by adjusting the distribution density of the light conversion particles 132 in the host material 131, it is also possible to generate light of one color or more than one color. For example, in the present disclosure, by reducing the distribution density of the light conversion particles 132 in the host material 131, the light emitted by the light emitting units 111 is not completely converted when passing through the light conversion layer 13; that is, by taking this embodiment as an example, part of the light passing through the light conversion layer 13 is not converted by the light conversion particles 132 and thus is still blue light, while the rest of the light is converted by the light conversion particles 1321, 1323 into near-infrared light and/or infrared light, but it is not limited thereto. In some embodiments, by increasing the distribution density of the light conversion particles 132 in the host material 131, the light emitted by the light emitting unit 111 can be completely converted when passing through the light conversion layer 13, so as to form, for example, single-color light different from the light emitted by the light emitting units 111, but it is not limited thereto.

The aforementioned adjustable structure 15 may be a structure of a liquid crystal layer or an electrophoretic array. By controlling the orientation of the liquid crystals or the color state of the electrophoretic particles with, for example, a controller (not shown), it is able to form a light penetrating area 151 and a non-penetrating area 153 on the adjustable structure 15, or the adjustable structure 15 may be controlled so that light may pass through its entire area, wherein the shape and size of the light penetrating area 151 are corresponding to the affected area 19. Accordingly, part of the light emitted by the light emitting units 111 and/or the converted light obtained from conversion of the light conversion layer 13 passes through the light penetrating area 151 of the adjustable structure 15 to irradiate the affected part 19 for phototherapy, while the rest of the light is blocked by the non-penetrating area 153 of the adjustable structure 15, and thus will not irradiate the human tissue other than the affected part 19, so as to avoid side effects on healthy areas. In addition, in this embodiment, on one side of the adjustable structure 15 facing the light conversion layer 13, that is, on one side of the adjustable structure 15 facing the light emitting layer 11, it may further provide a reflective structure 155 corresponding to the non-penetrating area. With the reflective structure 155, the light irradiated to the non-penetrating area 153 and/or the converted light may be reflected, and the reflected light and/or the converted light are then reflected by the substrate 201 to pass through the light penetrating area 151 to perform phototherapy, so as to fully utilize the light emitting efficiency of the light emitting units 111 thereby improving the effect of phototherapy.

Figure 2B:
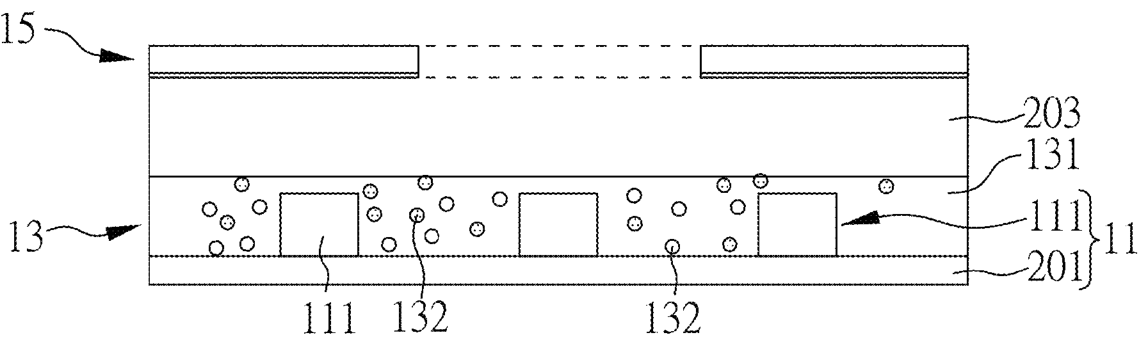
FIG. 2B shows another embodiment of the light emitting layer, the light conversion layer and the adjustable structure realized according to the electronic device of FIG. 1.

FIG. 2B shows another embodiment of the light emitting layer 11, the light conversion layer 13 and the adjustable structure 15 realized according to the electronic device of FIG. 1. The arrangement of the electronic device of this embodiment is similar to that of FIG. 2A, and thus the similar portions will not be described in detail while only the differences will be described below.

As shown in FIG. 2B, in this embodiment, the light emitting layer 11 still has a plurality of light emitting units 111 and a substrate 201, while the light conversion layer 13 including a host material 131 and light conversion particles 132 is arranged on the light emitting units 111 so as to convert the light emitted by the light emitting units 111 and simultaneously encapsulate the light emitting units 111. In addition, the connection layer 203 is arranged between the light conversion layer 13 and the adjustable structure 15, so that the light conversion layer 13 can be firmly connected to the adjustable structure 15.

Figure 2C:
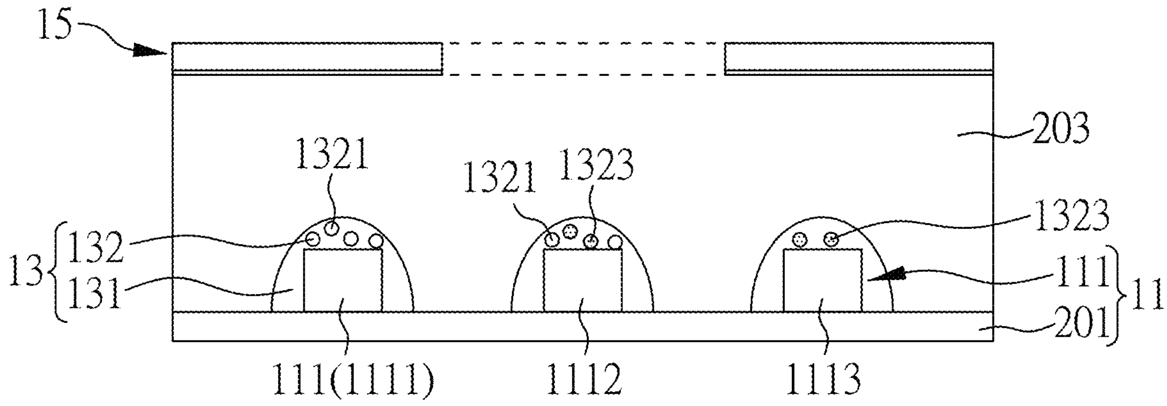
FIG. 2C shows still another embodiment of the light emitting layer, the light conversion layer and the adjustable structure realized according to the electronic device of FIG. 1.

FIG. 2C shows still another embodiment of the light emitting layer 11, the light conversion layer 13 and the adjustable structure 15 realized according to the electronic device of FIG. 1. The arrangement of the electronic device of this embodiment is similar to that of FIG. 2A, and thus the similar portions will not be described in detail while only the differences will be described below.

As shown in FIG. 2C, in this embodiment, the light emitting layer 11 still has a plurality of light emitting units 111 and a substrate 201, while the light conversion layer 13 including a host material 131 and light conversion particles 132 is separately arranged on the respective light emitting units 111 so as to convert the light emitted by the light emitting units 111 and simultaneously encapsulate the light emitting units 111. In addition, the connection layer 203 is arranged between the light conversion layer 13 and substrate 201 and the adjustable structure 15, so that the light conversion layer 13 and the substrate 201 can be firmly connected to the adjustable structure 15. In addition, in this embodiment, since the light emitting units 111 are individually encapsulated with the light conversion layer 13, the light conversion layer 13 encapsulating the light emitting units 111 may have light conversion particles 132 with different particle sizes, or may have light conversion particles 132 with reduced distribution density, so that the combination of the light emitting layer 11 and the light conversion layer 13 may provide light of various wavelengths. For example, in FIG. 2C, the light conversion layer 13 encapsulating the blue light emitting unit 1111 only has the light conversion particles 1321 with the same particle size, and thus may generate red light. The light conversion layer 13 encapsulating the blue light emitting unit 1112 has light conversion particles 1321, 1323 with different particle sizes, and thus may generate red light and near-infrared light. The light conversion layer 13 encapsulating the blue light emitting unit 1113 has light conversion particles 1323 with a low distribution density, and thus may generate blue light and near-infrared light.

Figure 2D:
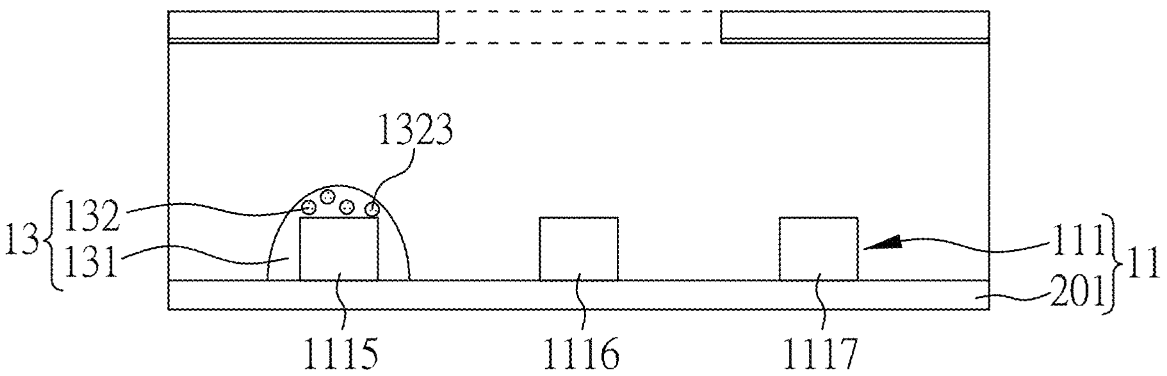
FIG. 2D shows yet another embodiment of the light emitting layer, the light conversion layer and the adjustable structure realized according to the electronic device of FIG. 1.

FIG. 2D shows yet another embodiment of the light emitting layer 11, the light conversion layer 13 and the adjustable structure 15 realized according to the electronic device of FIG. 1. The arrangement of the electronic device of this embodiment is similar to that of FIG. 2C, and thus the similar portions will not be described in detail while only the differences will be described below.

As shown in FIG. 2D, in this embodiment, the light emitting layer 11 still has a plurality of light emitting units 111 and a substrate 201, while the light conversion layer 13 including a host material 131 and light conversion particles 132 is only arranged on part of the light emitting units 111, such as the blue light emitting unit 1115 in FIG. 2D, and there is no light conversion layer 13 arranged on the rest of the light emitting units 111, such as the red light emitting units 1116, 1117 in FIG. 2D. Moreover, in FIG. 2D, the light conversion layer 13 encapsulating the blue light emitting unit 1115 has light conversion particles 1323, for example, and thus it may generate near-infrared light, while the red light generated by the red light emitting units 1116, 1117 is not subject to light conversion, so that, in this embodiment, the red light and near-infrared light are generated to perform phototherapy.

Figure 3:
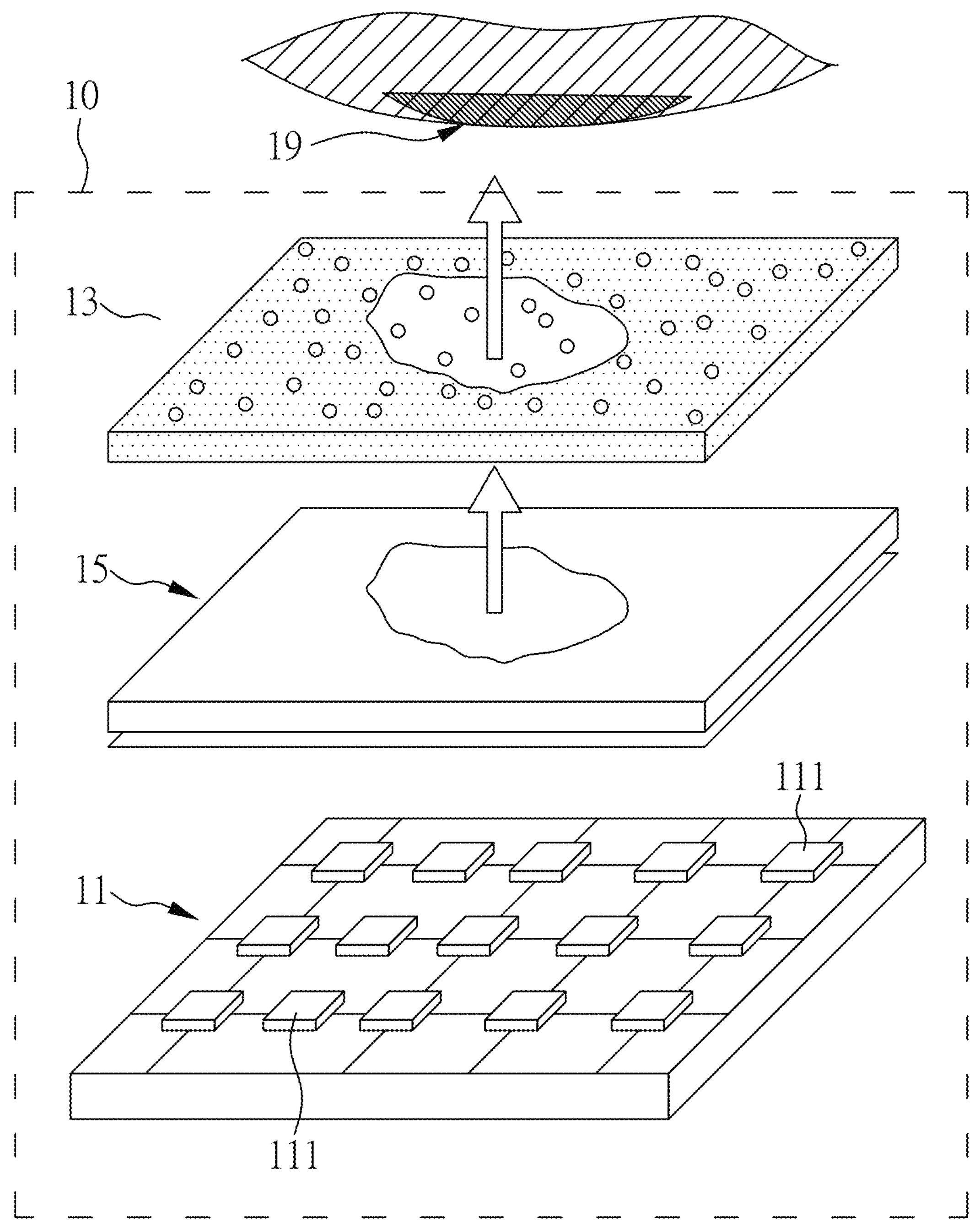
FIG. 3 is a schematic diagram of the electronic device according to another embodiment of the present disclosure.

FIG. 3 is a schematic diagram of an electronic device 10 according to another embodiment of the present disclosure. The electronic device 10 is used to treat an affected part 19. Similar to the embodiment of FIG. 1, the electronic device 10 of this embodiment includes a light emitting layer 11, a light conversion layer 13 and an adjustable structure 15, while the difference is that, in this embodiment, the aforementioned adjustable structure 15 is arranged between the light emitting layer 11 and the light conversion layer 13. That is, the adjustable structure 15 is disposed on the light emitting layer 11, the light emitting surface of the light emitting layer 11 faces the adjustable structure 15, and the light conversion layer 13 is disposed on the adjustable structure 15. Since the electronic device 10 of this embodiment differs from the embodiment of FIG. 1 only in the stacking positions of the light emitting layer 11, the light conversion layer 13 and the adjustable structure 15, the following description will focus on the differences caused by different stacking positions, while the portions with same features will not be repeated.

Figure 4:
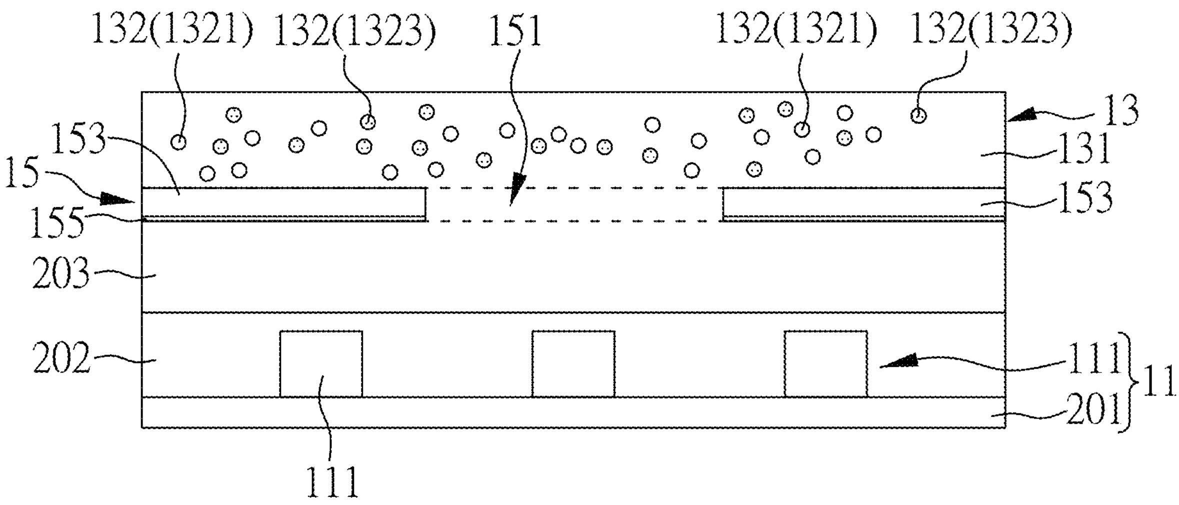
FIG. 4 shows an embodiment of the light emitting layer, the light conversion layer and the adjustable structure realized according to the electronic device of FIG. 3.

FIG. 4 shows an embodiment of the light emitting layer 11, the light conversion layer 13 and the adjustable structure 15 realized according to the electronic device of FIG. 3 of the present disclosure. As shown, in this embodiment, the light emitting layer 11 includes a plurality of light emitting units 111 and a substrate 201, wherein the plurality of light emitting units 111 are arranged on the substrate 201 in an array, for example. Furthermore, in order to protect the light emitting units 111, the present disclosure may further include an encapsulation layer 202 to encapsulate the light emitting units 111. In order to firmly connect the light emitting layer 11 and the encapsulation layer 202 to the adjustable structure 15, the present disclosure may further provide a connection layer 203 between the encapsulation layer 202 and the adjustable structure 15.

The aforementioned adjustable structure 15 may be a structure of a liquid crystal layer or an electrophoretic array, which may be controlled to form a light penetrating area 151 and a non-penetrating area 153, wherein the shape and size of the light penetrating area 151 are corresponding to the affected part 19. In addition, in this embodiment, on one side of the adjustable structure 15 facing the light emitting layer 11, it may further provide a reflective structure 155 corresponding to the non-penetrating area 153. With the reflective structure 155, the light irradiated on the non-penetrating area 153 may be reflected, and the reflected light is then reflected by the substrate 201 to pass through the light penetrating area 151 for conversion thereby fully utilizing the light emitting efficiency of the light emitting units. The aforementioned light conversion layer 13 includes a host material 131 and a plurality of light conversion particles 132 distributed in the host material 131. In this embodiment, by arranging light conversion particles 1321, 1323 with different particle sizes in the host material 131, it is able to generate converted light with different wavelengths. Accordingly, the light passing through the light penetrating area 151, such as blue light, may generate red light and/or near-infrared light for phototherapy after being converted by the light conversion layer 13 including light conversion particles 1321, 1323, but the present disclosure is not limited thereto.

Figure 5:
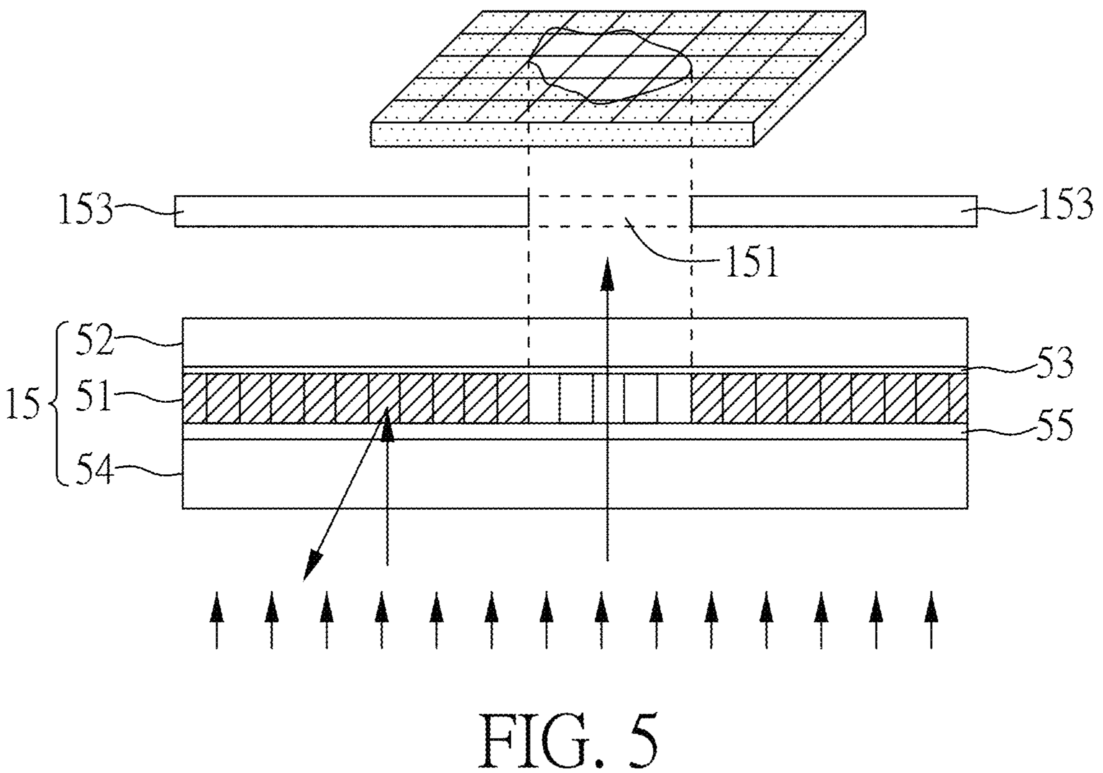
FIG. 5 is a schematic diagram of the adjustable structure according to an embodiment of the present disclosure.

FIG. 5 is a schematic diagram of the adjustable structure 15 according to an embodiment of the present disclosure. In this embodiment, the adjustable structure 15 is a structure of a liquid crystal layer. As shown, the adjustable structure 15 includes a first substrate 52, a second substrate 54, and a liquid crystal layer 51 sandwiched between the first substrate 52 and the second substrate 54. The liquid crystal layer 51 is formed by, for example, cholesteric liquid crystals arranged in a matrix. One side of the first substrate 52 facing the liquid crystal layer 51 is formed with a first electrode 53, and one side of the second substrate 54 facing the liquid crystal layer 51 is formed with a second electrode 55. With such a structure, by applying a driving voltage to the first electrode 53 and the second electrode 55, it is able to control the ON mode or OFF mode of the liquid crystals, thereby controlling the rotation angle of the liquid crystals, so that light may pass through the liquid crystal layer 51 or may be reflected by the liquid crystal layer 51. That is, the liquid crystals of the liquid crystal layer 51 corresponding to the light penetrating area 151 are driven to be on, so that the light emitted by the light emitting units 111 and/or the converted light obtained from conversion of the light conversion layer 13 may pass through the liquid crystals, while the liquid crystals of the liquid crystal layer 51 corresponding to the non-penetrating area 153 are driven to be off for use as the aforementioned reflective structure 155, so that the liquid crystals may reflect the light emitted by the light emitting units 111 and/or the converted light obtained from conversion of the light conversion layer 13 due to the rotation angle of the liquid crystals. Accordingly, it is able to realize the adjustable structure 15 that may be controlled to adjust the light penetrating area 151 to correspond to the affected part 19 to be treated.

Figure 6:
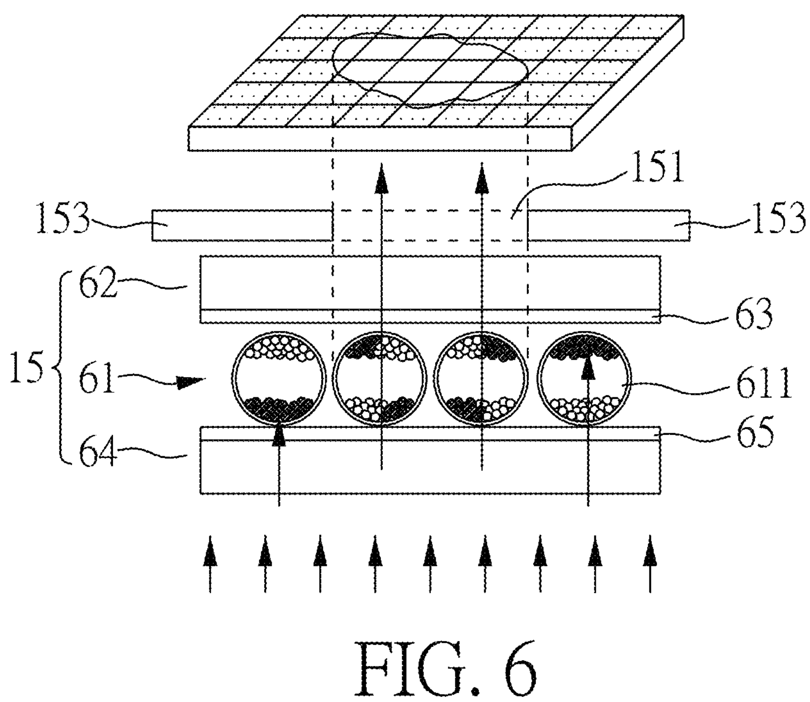
FIG. 6 is a schematic diagram of the adjustable structure according to another embodiment of the present disclosure.

FIG. 6 is a schematic diagram of an adjustable structure 15 according to another embodiment of the present disclosure. In this embodiment, the adjustable structure 15 is an electrophoretic array structure. As shown, the adjustable structure 15 includes a third substrate 62, a fourth substrate 64, and an electrophoretic array 61 sandwiched between the third substrate 62 and the fourth substrate 64. The electrophoretic array 61 is formed, for example, of microcapsules 611 arranged in a matrix. One side of the third substrate 62 facing the electrophoretic array 61 is formed with a third electrode 63, and one side of the fourth substrate 64 facing the electrophoretic array 61 is formed with a fourth electrode 65. With such a structure, by applying a driving voltage to the third electrode 63 and the fourth electrode 65, it is able to control the distribution of transparent electrophoretic particles and/or black electrophoretic particles in the microcapsule 611, so that light may pass through the electrophoretic array 61 or may be absorbed by the electrophoretic array 61. That is, the transparent particles are distributed in the microcapsules 611 of the electrophoretic array 61 corresponding to the light penetrating area 151 on the sides adjacent to the third electrode 63 and the fourth electrode 65, so that the light emitted by the light emitting units 111 and/or the converted light obtained from conversion of by the light conversion layer 13 may pass through the microcapsules 611, while the black particles are fully distributed in the microcapsule 611 of the electrophoretic array 61 corresponding to the non-penetrating area 153 on the side adjacent to the third electrode 63 or the fourth electrode 65, so that the light emitted by the light emitting units 111 and/or the converted light obtained from conversion of the light conversion layer 13 may be absorbed, thereby realizing the adjustable structure 15 that can be controlled to adjust the light penetrating area 151 to correspond to the affected part 19 to be treated.

Figure 7:
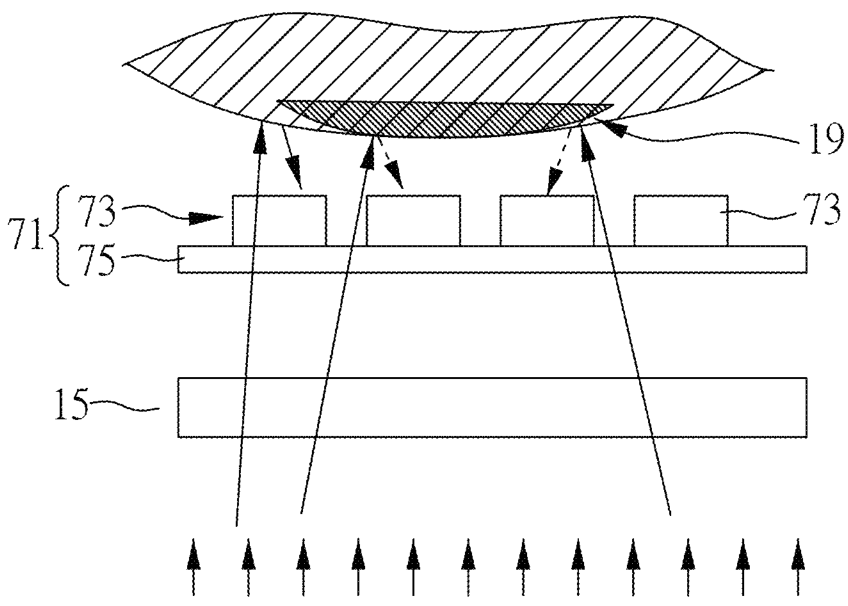
FIG. 7 schematically illustrates an embodiment of the present disclosure for determining the light penetrating area.

In addition, in order to control the adjustable structure 15 to precisely adjust the light penetrating area 151 to correspond to the affected part 19 to be treated, FIG. 7 schematically illustrates an embodiment of the present disclosure for determining the light penetrating area. As shown, the present disclosure further provides a light sensor array 71 to realize the determination of the light penetrating area 151. The light sensor array 71 may be arranged, for example, between the adjustable structure 15 and the treatment target (that is, the affected part 19), and the light sensor array 71 has a transparent substrate 75 and a plurality of light sensors 73 in a matrix form arranged on the transparent substrate 75. When detecting the light penetrating area 151, the adjustable structure 15 is controlled so that light may pass through its entire area. Therefore, the light emitted by the light emitting units 111 and/or the converted light obtained from conversion of the light conversion layer 13 may pass through the adjustable structure 15 and irradiate the affected part 19 through the gap between the light sensors 73 of the light sensor array 71, and then is reflected to the light sensors 73 by the affected part 19. Accordingly, the light sensor array 71 is able to detect the reflected light obtained from the light and/or the converted light irradiating the affected part 19, and adjust the adjustable structure 15 according to the detection result so as to form a light penetrating area 151 and a non-penetrating area 153. Because the formation of the light penetrating area 151 is obtained by directly detecting the affected part, the electronic device 10 of the present disclosure may perform phototherapy only on the shape of a specific target, thereby effectively avoiding side effects on healthy areas.

As long as the features of the various embodiments disclosed in the present disclosure do not violate the spirit of the invention or conflict with each other, they may be mixed and matched arbitrarily.

The aforementioned specific embodiments should be construed as merely illustrative, and not limiting the rest of the present disclosure in any way.

The invention claimed is:

1. An electronic device for treating an affected part, comprising:

a light emitting layer having a plurality of light emitting units for emitting light;

a light conversion layer for converting wavelength of light emitted by at least one of the light emitting units to provide converted light;

an adjustable structure controlled to adjust a light penetrating area to correspond to the affected part to be treated, wherein at least one of the light and the converted light passes through the light penetrating area to irradiate the affected part; and a light sensor array having a plurality of sensors for detecting reflected light obtained from at least one of the light and the converted light irradiating the affected part, based on which the adjustable structure is adjusted so as to form the light penetrating area and a non-penetrating area;

wherein the adjustable structure further includes a reflective structure corresponding to the non-penetrating area, and the reflective structure reflects at least one of the light and the converted light to pass through the light penetrating area.

2. The electronic device as claimed in claim 1, wherein the light conversion layer is disposed between the light emitting layer and the adjustable structure.

3. The electronic device as claimed in claim 2, wherein the light conversion layer includes a host material and a plurality of light conversion particles distributed in the host material, and the light emitting units are encapsulated by an encapsulation layer.

4. The electronic device as claimed in claim 3, wherein the plurality of light conversion particles include different types of light conversion particles.

5. The electronic device as claimed in claim 2, wherein the light conversion layer includes a host material and a plurality of light conversion particles distributed in the host material, and the light conversion layer encapsulates the light emitting units.

6. The electronic device as claimed in claim 2, wherein the light conversion layer includes a host material and a plurality of light conversion particles distributed in the host material, and the light conversion layer is separately arranged on the light emitting units, respectively, so as to individually encapsulate the light emitting units.

7. The electronic device as claimed in claim 6, wherein the light conversion layer encapsulating the light emitting units has light conversion particles with different particle sizes.

8. The electronic device as claimed in claim 2, wherein the light conversion layer includes a host material and a plurality of light conversion particles distributed in the host material, and the light conversion layer is separately arranged on part of the light emitting units, respectively, so as to individually encapsulate the part of the light emitting units.

9. The electronic device as claimed in claim 1, wherein the adjustable structure is disposed between the light emitting layer and the light conversion layer.

10. The electronic device as claimed in claim 9, further comprising: an encapsulation layer for encapsulating the light emitting units; and a connection layer arranged between the encapsulation layer and the adjustable structure.

11. The electronic device as claimed in claim 1, wherein the converted light includes light of two peak wavelengths.

12. The electronic device as claimed in claim 1, wherein the converted light has a wavelength in a range of 520 nm to 1100 nm.

13. The electronic device as claimed in claim 1, wherein, when the light sensor array detects the reflected light obtained from at least one of the light and the converted light irradiating the affected part, the adjustable structure is controlled so that light passes through entire area of the adjustable structure.

14. The electronic device as claimed in claim 1, wherein the adjustable structure has a cholesteric liquid crystal layer.

15. The electronic device as claimed in claim 14, wherein the adjustable structure includes a first substrate, a second substrate, and the cholesteric liquid crystal layer sandwiched between the first substrate and the second substrate, in which a first electrode is formed on one side of the first substrate facing the cholesteric liquid crystal layer, and a second electrode is formed on one side of the second substrate facing the cholesteric liquid crystal layer.

16. The electronic device as claimed in claim 1, wherein the adjustable structure has an electrophoretic array.

17. The electronic device as claimed in claim 16, wherein the adjustable structure 15 includes a third substrate, a fourth substrate, and the electrophoretic array sandwiched between the third substrate and the fourth substrate, in which a third electrode is formed on one side of the third substrate facing the electrophoretic array, and a fourth electrode is formed on one side of the fourth substrate facing the electrophoretic array.

18. The electronic device as claimed in claim 1, wherein the light sensor array has a transparent substrate and the plurality of light sensors are arranged in a matrix on the transparent substrate.

* * * * *